United States Patent
Daniels et al.

(10) Patent No.: US 11,653,956 B2
(45) Date of Patent: May 23, 2023

(54) CROSS CONNECTION SYSTEM FOR STRENGTHENING A STABILIZATION CONSTRUCT

(71) Applicant: Quandary Medical, LLC, Wilmington, NC (US)

(72) Inventors: Alan Daniels, Barrington, RI (US); Miles Wilson, Tiverton, RI (US)

(*) Notice: Subject to any disclaimer, the term of this patent is extended or adjusted under 35 U.S.C. 154(b) by 0 days.

(21) Appl. No.: 16/684,171

(22) Filed: Nov. 14, 2019

(65) Prior Publication Data

US 2020/0146728 A1 May 14, 2020

Related U.S. Application Data

(60) Provisional application No. 62/767,453, filed on Nov. 14, 2018.

(51) Int. Cl.
*A61B 17/70* (2006.01)

(52) U.S. Cl.
CPC ...... *A61B 17/7052* (2013.01); *A61B 17/7002* (2013.01); *A61B 17/7034* (2013.01); *A61B 17/7037* (2013.01)

(58) Field of Classification Search
CPC ............ A61B 17/7052; A61B 17/7049; A61B 17/7032; A61B 17/7034; A61B 17/7026; A61B 17/7031
USPC ...................................................... 606/250
See application file for complete search history.

(56) References Cited

U.S. PATENT DOCUMENTS

| | | | |
|---|---|---|---|
| 5,667,506 A * | 9/1997 | Sutterlin | A61B 17/7049 606/252 |
| 5,702,392 A * | 12/1997 | Wu | A61B 17/7043 606/264 |
| 6,887,241 B1 * | 5/2005 | McBride | A61B 17/7049 606/252 |
| 7,160,301 B2 * | 1/2007 | Cordaro | A61B 17/7049 606/86 A |
| 8,226,689 B2 * | 7/2012 | Jones | A61B 17/7049 606/276 |
| 8,372,120 B2 * | 2/2013 | James | A61B 17/7052 606/250 |
| 8,556,942 B2 * | 10/2013 | Ziolo | A61B 17/7055 606/280 |
| 9,131,963 B2 * | 9/2015 | Predick | A61B 17/7049 |
| 9,283,001 B2 * | 3/2016 | Harper | A61B 17/7043 |
| 9,814,493 B2 * | 11/2017 | Pham | A61B 17/7052 |
| 10,398,476 B2 * | 9/2019 | Lee | A61B 17/7049 |
| 2003/0105460 A1 * | 6/2003 | Crandall | A61B 17/7041 606/279 |
| 2006/0247626 A1 * | 11/2006 | Taylor | A61B 17/7049 606/252 |
| 2007/0083201 A1 * | 4/2007 | Jones | A61B 17/7049 606/252 |

(Continued)

*Primary Examiner* — Nicholas J Plionis
(74) *Attorney, Agent, or Firm* — Hall Estill Law Firm

(57) ABSTRACT

A system is utilized, which comprises a cross connector for use in spinal fixation, further comprising multiple connection features configured to accommodate for direct attachment to multiple rods. Teachings are directed to a device that not only provides increased construct stiffness in flexion, extension and lateral bending, but also in torsion. The system adds stiffness in standard constructs. Joining multiple adjacent constructs with varying rod sizes for load distribution are also benefits of the system.

18 Claims, 8 Drawing Sheets

(56) References Cited

U.S. PATENT DOCUMENTS

| | | | |
|---|---|---|---|
| 2008/0021454 A1* | 1/2008 | Chao | A61B 17/7044 606/250 |
| 2008/0021456 A1* | 1/2008 | Gupta | A61B 17/7049 606/250 |
| 2009/0177234 A1* | 7/2009 | Butler | A61B 17/7052 606/264 |
| 2010/0094345 A1* | 4/2010 | Saidha | A61B 17/7052 606/250 |
| 2011/0087287 A1* | 4/2011 | Reeder, Jr. | A61B 17/7011 606/264 |
| 2013/0006307 A1* | 1/2013 | Robinson | A61B 17/8695 606/252 |
| 2013/0184762 A1* | 7/2013 | Harper | A61B 17/7043 606/279 |
| 2016/0367292 A1* | 12/2016 | Nichols | A61B 17/7041 |

* cited by examiner

CROSS CONNECTION SYSTEM FOR STRENGTHENING A STABILIZATION CONSTRUCT

CROSS REFERENCE TO RELATED APPLICATIONS

This application is a conversion application of U.S. Provisional Patent Application 62/767,453, filed on Nov. 14, 2018, which is hereby incorporated by reference.

FIELD OF THE INVENTION

The present invention relates to spinal fixation devices, and in particular to a cross connector for connecting spinal fixation elements, such as spinal fixation rods, implanted in a patient's spinal system.

BACKGROUND OF THE INVENTION

Screws, rods, plates, and connectors are generally used to build a metal structure attached to the bony tissue preventing significant movement. In procedures involving bone fusion, the metal structure is attached in order to allow the bone to stabilize and fuse together during the healing process.

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

In cases where patients must undergo bone fusion in association with long segmental spine fusions, additional stabilization rods often are necessary. In these situations, rod attachment clips are implanted to allow a second rod to be installed adjacent to the initial rod. This adds time, metal, cost, and complexity to the operative procedure.

One of the conventional methods for fixating the vertebrae during the healing and fusion process is to use pedicle screws inserted through the bony pedicle anatomy of spine vertebrae and into the vertebral body. The conventional pedicle screw may include a head device with a connection feature commonly referred to as a "tulip" to hold cylindrical rods. Such screw/rod constructs rigidly hold the vertebrae bones to prevent motion during the healing process.

Cross connector implants are often used in conjunction with spinal fixation devices to provide additional stability to the devices. For example, it has been found that when a pair of spinal rods are fastened in parallel on either side of the spinous process, the assembly can be significantly strengthened by using a cross connector to bridge the pair of spinal rods. The connectors are typically in the form of a rod having a clamp formed on each end thereof for mating with a spinal rod.

While current spinal cross connectors have proven effective, difficulties have been encountered in mounting the cross connectors, and maintaining them in a desired position and orientation with respect to the spinal rod, or other spinal fixation device or plurality of spinal fixation devices to which they are attached. In particular, the clamp assemblies often consist of several parts which make surgical application tedious, and which can also increase the manufacturing costs. Since the cross connector is often applied as the last step in a lengthy surgical procedure, ease of application is paramount. Fixation of the cross connector to one or more spinal rods can also be difficult in cases where a plurality of rods are not parallel to one another (diverging/converging with respect to one another), or out of plane with each other.

Cross connector implants between two parallel rods often are utilized to add additional rotational stability to the screw/rod construct. A challenge, however, is that many related systems are designed specifically for two single rods of a particular size installed on opposite sides of the posterior spine. Engineers and surgeons have explored other solutions, including the implantation of larger metal rods, in order to minimize the incidence of rod breakage. However, challenges remain, and such systems necessitate improvement before adapting to such improvement to minimize rod breakage.

A problem often encountered requiring the implementation of a cross connector relates to the sizing of rods. Many fusion constructs with low diameter rods fail. Specifically, fusion constructs incorporating one 5.5 millimeter or one 6.0 millimeter rod fail due to excessive loads placed upon the rod. This requires the placement of additional replacement or supplementary rods. Such placement may further require the joining of constructs comprising rods of different rod diameters.

Another problem often encountered during spinal fusion relates to adjacent level constructs. Adjacent level constructs can be unstable. Moreover, adjacent level constructs may produce high moment arms. Such challenges increase the load placed upon rods in spinal stabilization constructs.

Additionally, recent improvements purport to increase the rigidity of the spinal stabilization constructs by utilizing more than two single rods in association with screw/rod constructs. One mechanism relied upon to accomplish such improvement is commonly referred to as a dual rod "domino." The domino incorporates a slot that receives one rod and a second slot that received a second rod. It has been demonstrated in flexural bench testing and clinically that this additional rigid rod significantly increases the stiffness of the construct and reduces the flexural fatigue of the elements, thereby possibly reducing pseudo arthrosis and eliminating rod breakage during the life of the patient. However, the domino structure has exhibited a number of drawbacks. Publications highlighting the challenges associated with usage of the domino include JNeurosurg Spine 21:994-1003, 2014: Prospective multicenter assessment of risk factors for rod fracture following surgery for adult spinal deformity. In the patients studied, 18/200 (9%) of patients experienced rod fracture within the 24 months post-surgery with an even higher rate of 22% rod fracture rate in patients undergoing spinal osteotomy.

Accordingly, a need exists for improved spinal cross connectors that can accommodate more than two laterally placed rods.

SUMMARY

In one embodiment of the present disclosure, a system is utilized, which comprises a cross connector for use in spinal fixation, further comprising multiple connection features configured to accommodate for direct attachment to multiple rods. Teachings of the disclosure are directed to device that not only provides increased construct stiffness in flexion, extension and lateral bending, but also in torsion. This embodiment of the disclosure adds stiffness in standard constructs. This embodiment of the disclosure also allows for joining multiple adjacent constructs with varying rod sizes for load distribution.

BRIEF DESCRIPTION OF THE FIGURES

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present disclosure generally provides various methods and devices for connecting more than two spinal fixation elements 1024, such as spinal rods, implanted in a patient's spinal column. In general, each cross connector is configured, optionally as a bar arm 1015, to receive and engage at least three, and more preferably four spinal fixation elements 1024. The cross connectors can include various features to facilitate such engagement. In certain exemplary embodiments, the cross connectors can be adjustable to facilitate loading and mating of the cross connector onto at least three spinal fixation elements 1024 implanted in a patient's spinal column in accordance with methods well recognized by those skilled in the art.

Figure 1:
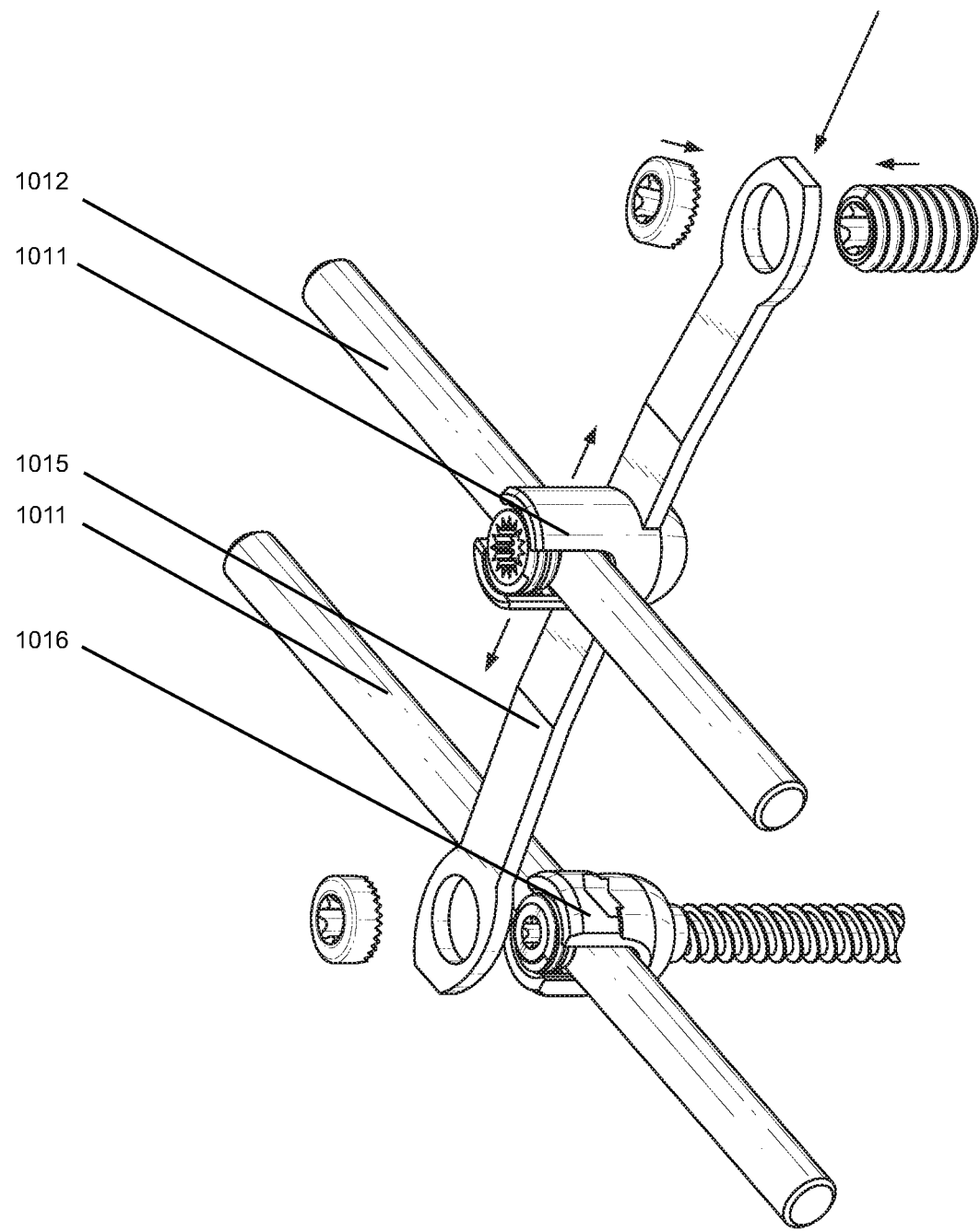
FIG. 1 depicts an embodiment of the invention comprising a partially disassembled construct further comprising a third rod attached to at least one bar arm via a tulip head configured to translate laterally along the at least one bar arm.
Figure 2:
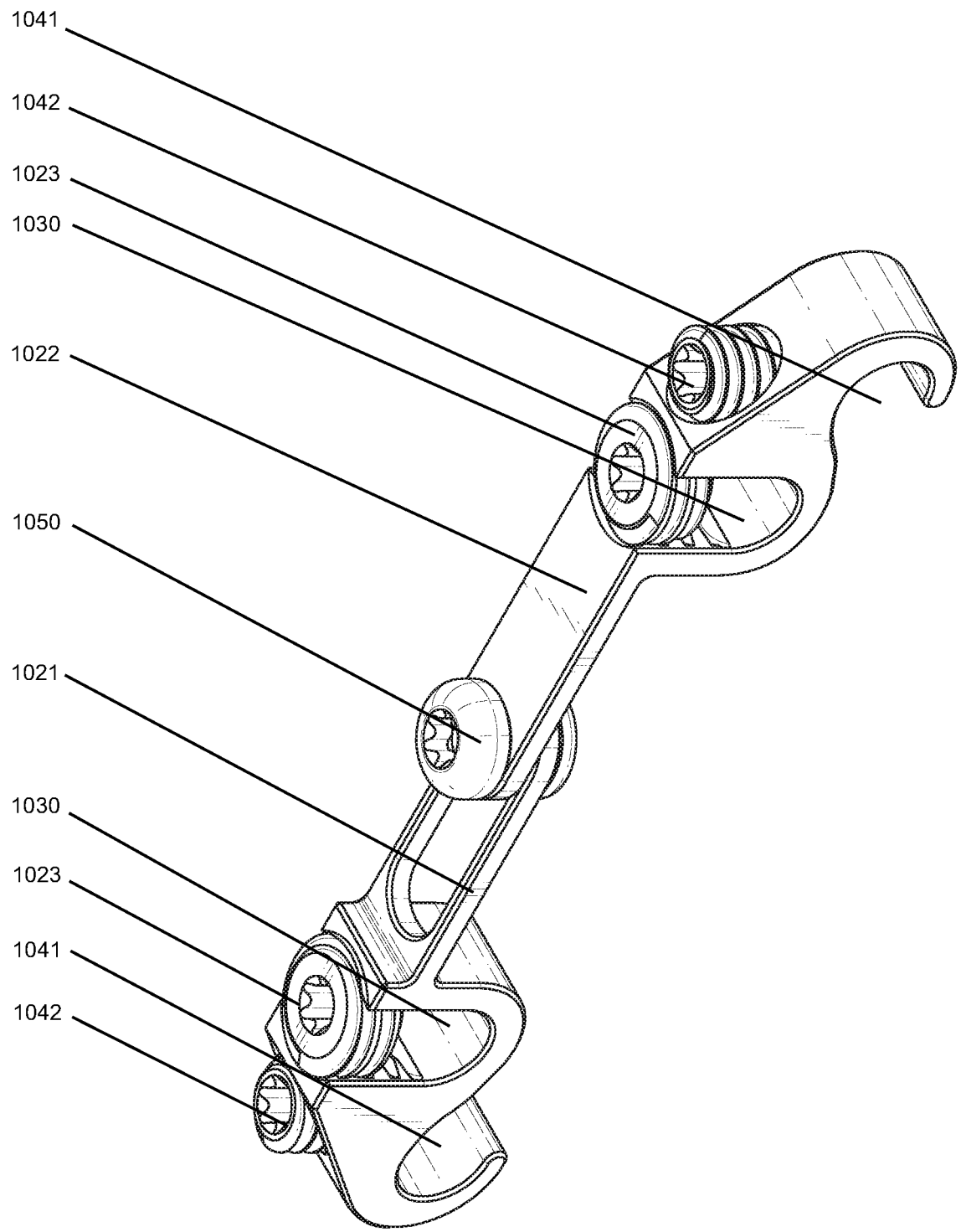
FIG. 2 depicts an embodiment of the bar arm.

For example, in an embodiment shown in FIG. 1, at least one tulip head 1010 placed on the bar arm 1015 is configured to translate laterally along the bar arm 1015, such that the positioning of the at least one tulip head 1010, and optionally one or more additional tulip heads 1010, can be adjusted to accommodate spinal fixation elements 1024 positioned medially in relation to the laterally placed rods 1011 at various distances relative to one another. The bar arm 1015 is configured to affix into pedicle screw tulip heads 1016. In certain embodiments, the bar arm 1015 consists of a fixed length.

In another embodiment of the present disclosure shown in FIGS. 2-6, the bar arm 1015 consists of two members, an elongated aperture member 1021 and a circular aperture bar arm member 1022, axially rotatable and/or pivotable relative to one another. In an embodiment, once the desired position of the elongated aperture member 1021 and the circular aperture bar arm member 1022 is configured, the construct is tightened with a pivot point screw, nut and washer system 1050. In various embodiments, the pivot point screw, nut and washer system 1050 may comprise a variety of alternatives, including replacing the nut and washer elements of the system with threading directly into an element of the bar arm 1015. The bar arm 1015 in such configuration thus accommodates spinal fixation elements 1024, for example a plurality of rods, residing in different planes and/or extending at various angles (i.e., converging or diverging) relative to one another. In such configuration, the bar arm 1015 optionally retains at least one spinal fixation element 1024 by surrounding it with a u-shaped recess 1030 incorporating threading further featuring a set screw 1023 screwed into the u-shaped recess 1030 to tighten the at least one spinal fixation element 1024 by methods well understood by those skilled in the art.

Figure 3:
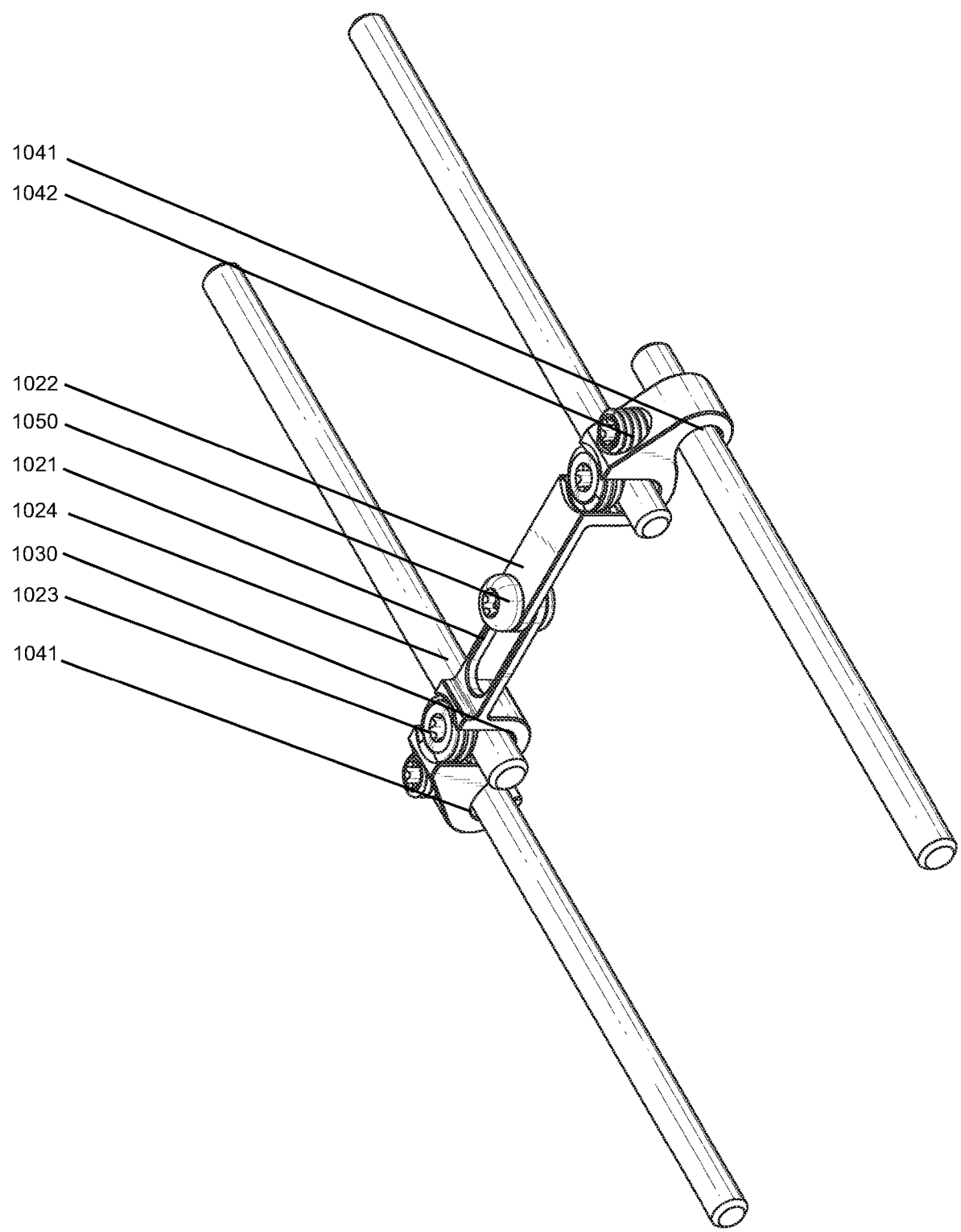
FIG. 3 depicts an assembled construct of an embodiment of the invention.
Figure 4:
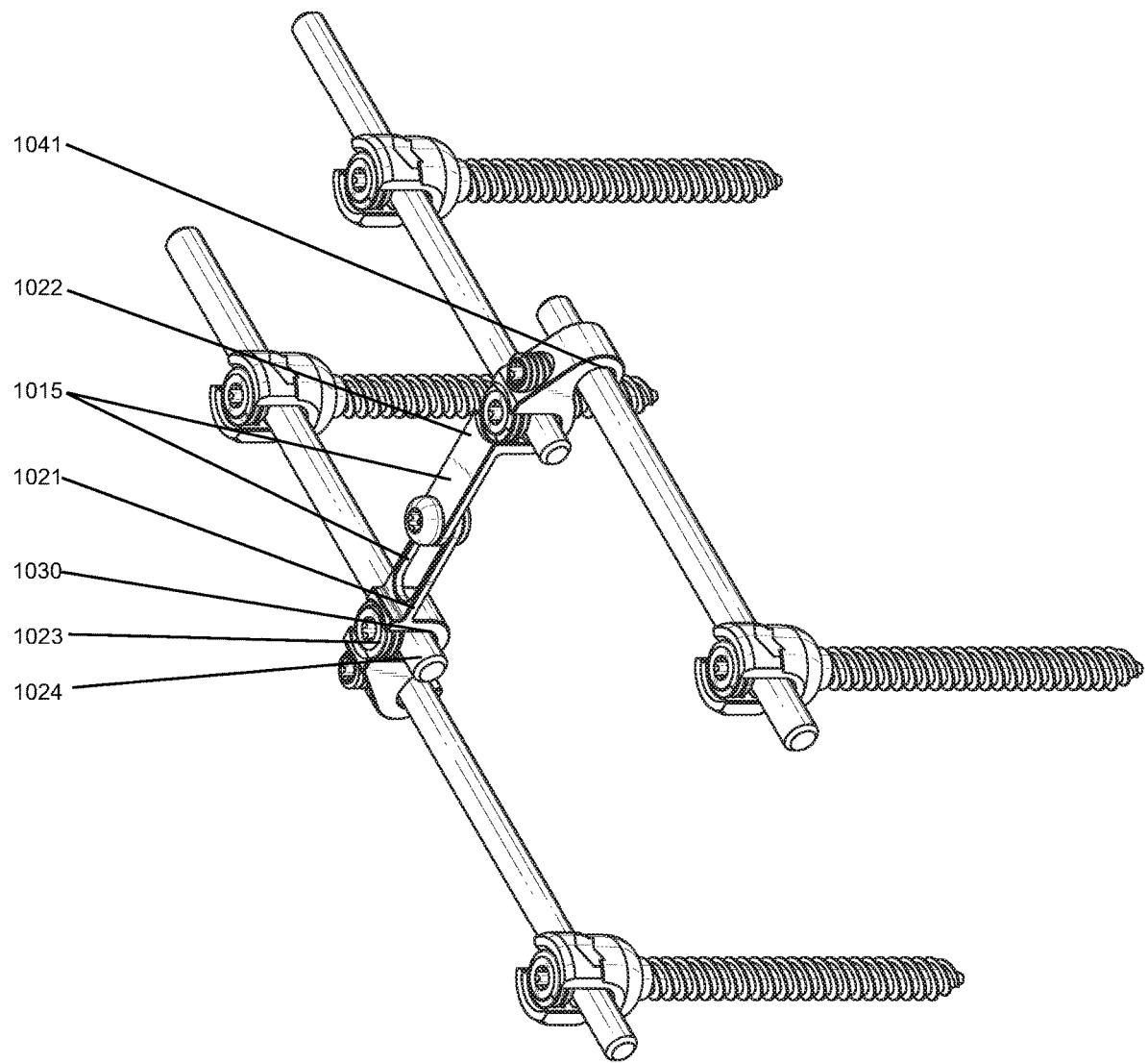
FIG. 4 depicts an assembled construct of an embodiment of the invention further comprising pedicle screws.
Figure 5:
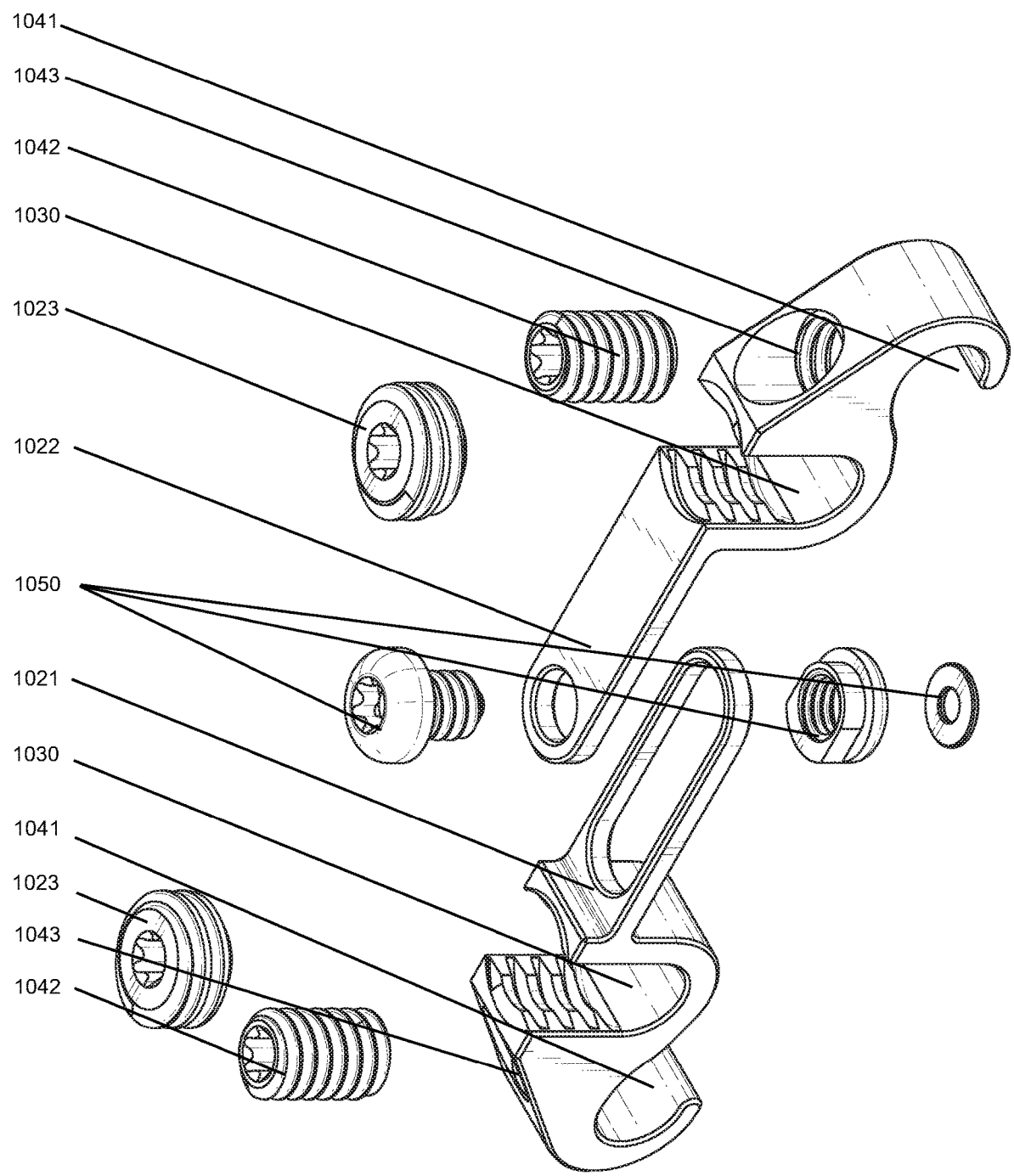
FIG. 5 depicts a disassembled embodiment of the bar arm and associated components.
Figure 6:
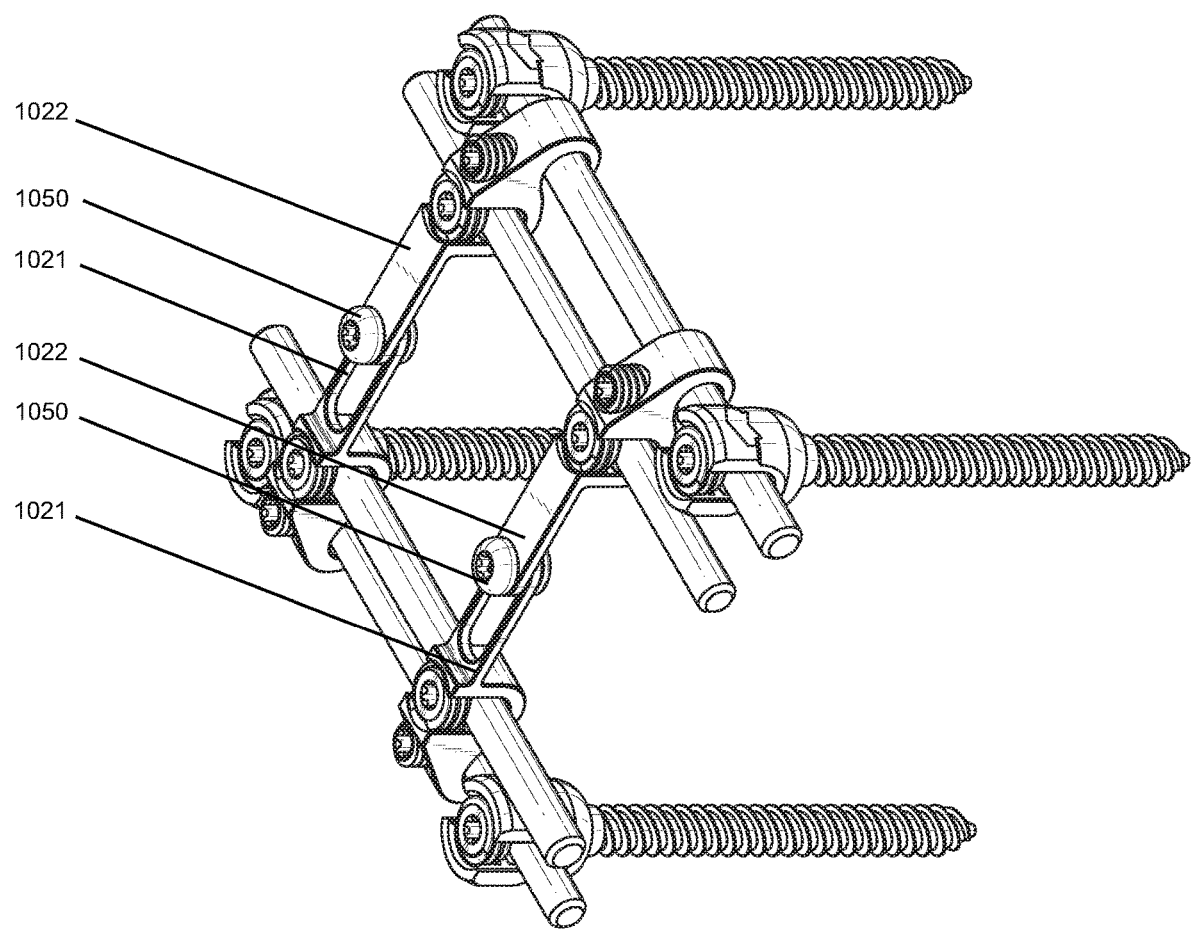
FIG. 6 depicts an assembled construct of an embodiment of the invention comprising a plurality of bar arms.

In an embodiment, the bar arm 1015 is configured to facilitate simultaneous top-loading of the bar arm 1015 onto at least one spinal fixation element 1024. In such embodiment, the bar arm 1015 incorporates at least one underside recess 1041. The underside recess 1041 is configured in substantially a cross-sectional shape of the letter "U" or the letter "C" in an embodiment. In another embodiment, the underside recess 1041 facilitates placement the bar arm 1015 to be placed on top of one or more spinal fixation elements 1024 already installed into a human body. For each underside recess 1041 there can be a threaded aperture 1043 configured to accommodate a top tightening screw 1042. In association with the method of use of a bar arm 1015 configured to comprise one or more underside recesses 1041, a user engages in a step of placing the bar arm 1015 over one or more spinal fixation elements 1024 already installed into a human body, and aligning the underside recesses 1041 such that the one or more underside recesses 1041 substantially surrounds one or more spinal fixation elements 1024, as depicted in FIG. 3. Following placement, for each underside recess 1041, a top tightening screw 1042 is placed through a hole substantially superior to the underside recess 1041 and tightened to grip the corresponding spinal fixation element 1024 in accordance with methods well understood by those skilled in the art, resulting in the fixation of the bar arm 1015 onto one or more spinal fixation elements 1024 already installed into a human body.

A person skilled in the art will appreciate that one or more cross connectors, which may comprise a plurality of bar arms 1015, are described herein as being adapted to engage a spinal fixation element 1024, and in particular a spinal fixation rod, can be implemented. In various embodiments the spinal fixation elements 1024 that the bar arm 1015 is configured to engage comprise laterally placed rods 1011 and spinal fixation elements 1024 positioned medially. The cross connectors can be configured to engage a variety of spinal fixation devices, such as anchors, cables, fixation plates, etc. Moreover, the one or more cross connectors can be configured to engage any number of spinal fixation elements 1024, including only a single spinal fixation element 1024. In such embodiment configured to engage a single spinal fixation element 1024, the one or more cross connectors engage either a laterally placed rod 1011 or a spinal fixation element 1024 positioned medially. In various embodiments, one or more opposed terminal ends of the cross connector 1070 can be adapted for other uses. For example, at least one opposed terminal end of the cross connector 1070 is configured to be fixedly attached to a vertebra. The cross connectors of the present disclosure can also include any combination of features described and/or illustrated herein, and the cross connectors are not limited to having the configuration shown in the illustrated embodiments.

Figure 7:
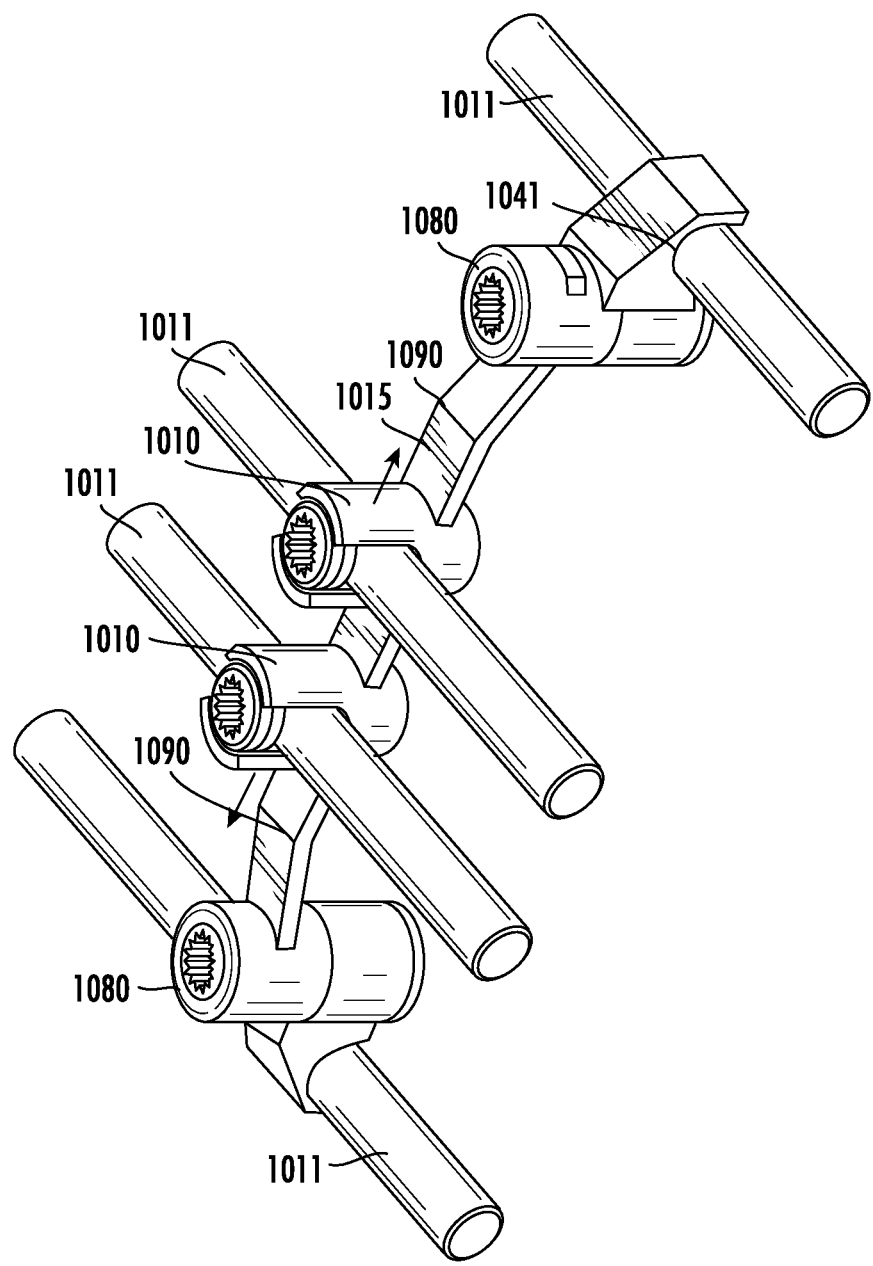
FIG. 7 depicts an embodiment of the invention comprising a construct featuring a plurality of rods each attached to at least one bar arm via one of a plurality of tulip heads each configured to translate laterally along the bar arm.
Figure 8:
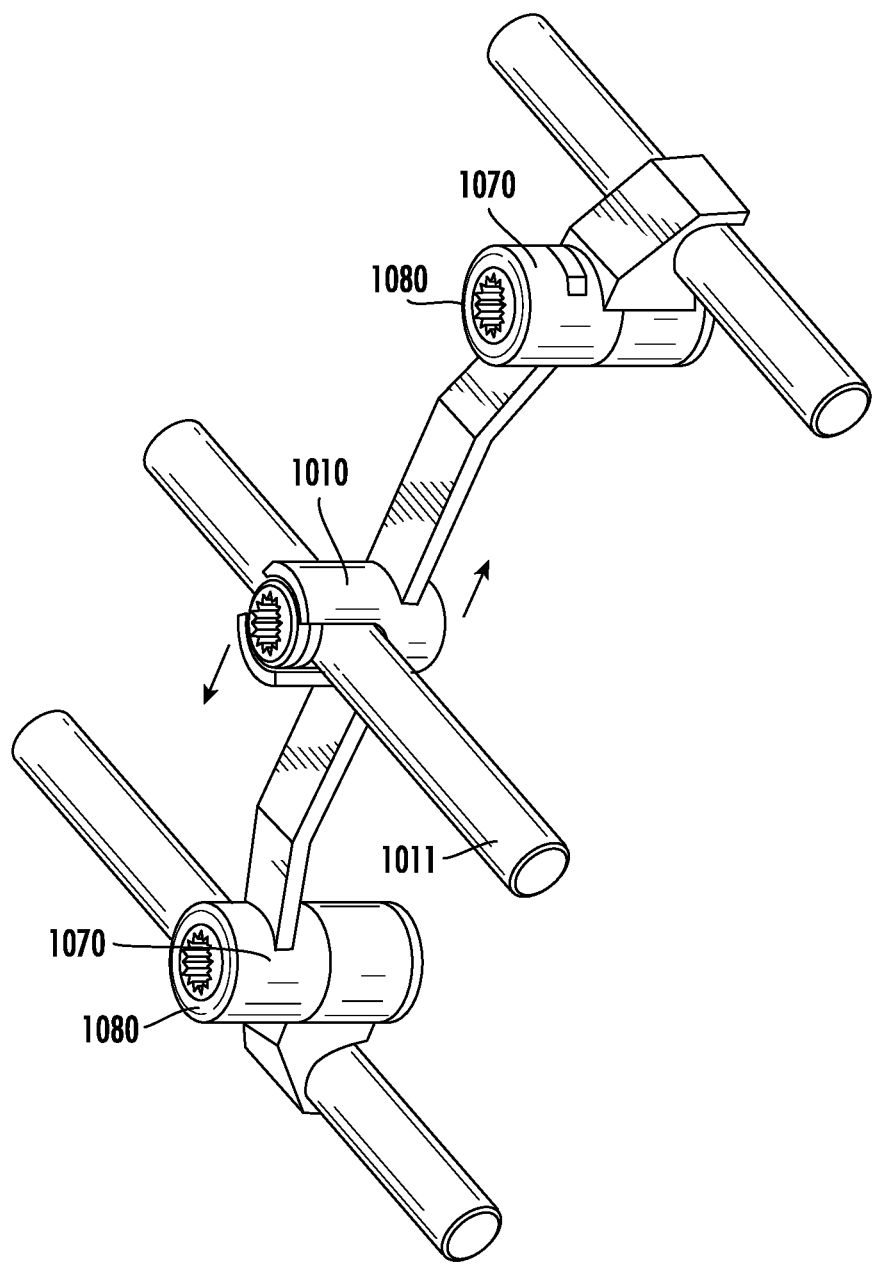
FIG. 8 depicts an embodiment of the invention comprising a construct further comprising a third rod attached to at least one bar arm via a tulip head configured to translate laterally along the at least one bar arm.

In various embodiments, the cross connector is configured to accommodate three rods, as depicted in FIG. 8, or four rods, as depicted in FIG. 7. During certain uses, the system may be installed during the index surgery, or attached to previously placed and/or newly revised constructs during revision surgery. The appropriately chosen time for installation will be readily understood by one skilled in the art.

In one embodiment, the disclosure consists of a system comprising at least two laterally placed cross connectors 1070, each comprising: a pivot point screw 1080, nut and washer system 1050; at least one tulip head 1010; at least one bar arm 1015, a plurality of pedicle screws 1016; at least one laterally placed rod 1011; and at least one set screw 1023. In certain embodiments, the cross connector 1070 is configured to comprise two lateral rod attachment sites.

The cross connector 1070 is optionally connected by a first bar arm 1015 comprising a connection point for a third rod. The connection point for the third rod is configured as a tulip head 1010 that translates laterally along the first bar arm 1015, as depicted in FIG. 1. The two lateral rod attachment sites of the first bar arm 1015, each optionally consisting of an underside recess 1041 and a top tightening screw 1042, are configured to each accommodate another bar arm 1015. The other bar arm 1015 creating a connection between a first bar arm 1015 and a separate third bar arm 1015.

In a further embodiment of the present disclosure, the tulip head 1010 comprises a monoaxial tulip in a low profile configuration. In an embodiment, the tulip head 1010 is configured to translate laterally along a bar arm 1015. In an embodiment, the tulip head 1010 is configured to provide increased construct stiffness in flexion, extension and lateral bending, and also in torsion. The present disclosure contemplates that configurations of an embodiment as presented herein incorporating a tulip head 1010 allow for joining multiple adjacent constructs with varying rod sizes for load distribution, which is incorporated as a teaching of the invention. In embodiments, the tulip head 1010 is configured of a shape to engage 05.5 mm or 06.0 mm rods, as known in the art. In an embodiment, the tulip head 1010 is configured to retain a rod in two points of contact.

In another embodiment, a third rod connection point is configured to attach to a post. Such configuration allows the tulip head 1010 to rotate and move side to side in a rotational manner.

In a further embodiment, the cross connector 1070 is configured to comprise two lateral rod attachment sites, each optionally consisting of an underside recess 1041. In such embodiment, the two lateral rod attachment sites are connected by a bar arm 1015 that has a third rod connection point, optionally comprising a tulip head 1010, and a fourth rod connection point, also optionally comprising a tulip head 1010. In an embodiment, the third rod connection point and fourth rod connection point comprising tulip heads 1010 are each configured to translate along the bar arm 1015 as depicted in FIG. 7. The bar arm 1015 shown in FIGS. 7 and 8 includes one or more other features to facilitate adjustability, such as one or more bend zones 1090.

In various embodiments, a cross connector 1070 comprising a combination of all or part of the aforementioned features is a teaching of the disclosure. In various embodiments, the cross connector 1070 is configured to have a polyaxial tulip head 1010, or mono axial tulip head 1010, configured to translate along the bar arm 1015.

The present disclosure also provides various exemplary methods for implanting a cross connector 1070. In one exemplary embodiment, the various cross connectors 1070 disclosed herein can be coupled to three or more, and preferably four, spinal fixation elements 1024, such as spinal rods, that are implanted within a patient's spine. Prior to loading the cross connector 1070 onto first and second laterally positioned rods 1011, the set screw 1023 and/or top tightening screw 1042 are not yet tightened onto the laterally positioned rods 1011 or spinal fixation elements 1024 positioned medially. The cross connector 1070 is then advanced toward laterally positioned rods 1011 already in place, which optionally are previously implanted in the spine such that they generally extend longitudinally along a length of the spinal column. Due to the parallel configuration of the one or more underside recesses 1041, each cross connector 1070 can be simultaneously loaded onto the one or more laterally positioned rods 1011. In one embodiment of the present disclosure, only one laterally positioned rod 1011 is incorporated, thus only one underside recess 1041 is incorporated.

In yet another embodiment, a third rod and optionally a fourth rod are then placed by the surgeon into at least one tulip head 1010 configured to translate along the bar arm 1015, which is placed medially from the laterally positioned rods 1011. Depending on the particular configuration, the cross connector 1070 can also be adjusted by deforming the bend zone 1090 located within the bar arm 1015 in an embodiment of the invention. Once the cross connector 1070 is properly positioned over the laterally positioned rods 1011, specifically by positioning the one or more laterally positioned rods 1011 within the one or more underside recesses 1041, for example as depicted in FIG. 7, and at least the third rod and optionally the fourth rod are placed into the one or more tulip heads 1010 as depicted in FIG. 7, the locking mechanisms optionally comprising one or more set screws 1023 and/or one or more top tightening screws 1042 can be fully tightened to place pressure upon each of the spinal fixation elements 1024.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. The benefits, advantages, solutions to problems, and any element (s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The terms "coupled" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence.

What is claimed is:

1. A cross connector system, comprising:
   a bar arm;
   a first laterally placed cross connector supported by a first end of the bar arm, the first laterally placed cross connector configured to accommodate and retain a first rod;
   a second laterally placed cross connector supported by a second end of the bar arm, the second laterally placed cross connector configured to accommodate and retain a second rod, the first or second laterally placed cross connector rotatable and can have numerous secured positions relative to the bar arm, the first and second laterally placed cross connectors positioned in a first plane in a first direction prior to the cross connector system being manipulated by a user; and
   at least one tulip head secured to the bar arm and configured to translate laterally and rotate to accommodate a third rod in an upwardly-facing recess of the at least one tulip head, the at least one tulip head positioned in a second plane in the first direction that is parallel to the first plane,
   wherein the first laterally placed cross connector includes a first downwardly-facing recess disposed on a lower side of the first laterally placed cross connector, the first downwardly-facing recess on the lower side configured to receive the first rod.

2. The cross connector system of claim 1 wherein the bar arm includes a second tulip head secured thereto.

3. The cross connector system of claim 2 wherein the second tulip head is configured to translate laterally and rotate to accommodate a fourth rod.

4. The cross connector system of claim 2 wherein the second tulip head is positioned in the second plane in the first direction prior to cross connector system being manipulated by a user.

5. The cross connector system of claim 1 further comprising at least one pedicle screw secured to the first, second or third rod.

6. The cross connector system of claim 1 wherein the bar arm includes at least one bend zone disposed therein.

7. The cross connector system of claim 1 wherein the second laterally placed cross connector includes a second recess disposed on a lower side of the second laterally placed cross connector, the second recess on the lower side configured to receive the second rod.

8. The cross connector system of claim 1 wherein the first laterally placed cross connector, the second laterally placed cross connector, and the at least one tulip head are positioned in separate, parallel planes in a second direction.

9. The cross connector system of claim 8 wherein the first laterally placed cross connector, the second laterally placed cross connector, and the at least one tulip head are positioned in a single plane in a third direction prior to the cross connector system being manipulated by the user.

10. A method of implanting a cross connector system, the method comprising:
    coupling a first laterally placed cross connector disposed on a first end of a bar arm to a first rod implanted within a patient's spine;
    coupling a second laterally placed cross connector disposed on a second end of the bar arm to a second rod implanted within a patient's body, the first or second laterally placed cross connector rotatable and can have numerous secured positions relative to the bar arm, the first and second laterally placed cross connectors positioned in a first plane in a first direction prior to the cross connector system being manipulated by a user; and
    securing a first tulip head to the bar arm, the first tulip head configured to translate laterally and rotate to accommodate a third rod in an upwardly-facing recess of the first tulip head, the first tulip head positioned in a second plane in the first direction that is parallel to the first plane,
    wherein the first laterally placed cross connector includes a first downwardly-facing recess disposed on a lower side of the first laterally placed cross connector, the first downwardly-facing recess on the lower side configured to receive the first rod.

11. The method of claim 10 wherein the bar arm includes a second tulip head secured thereto.

12. The method of claim 11 wherein the second tulip head is configured to translate laterally and rotate to accommodate a fourth rod.

13. The method of claim 11 wherein the second tulip head is positioned in the second plane in the first direction prior to cross connector system being manipulated by a user.

14. The method of claim 10 wherein the second laterally placed cross connector includes a second recess disposed on a lower of the second laterally placed cross connector, the second recess on the lower side configured to receive the second rod.

15. The method of claim 10 further comprising at least one pedicle screw secured to the first, second or third rod.

16. The method of claim 10 wherein the bar arm includes at least one bend zone disposed therein.

17. The method of claim 10 wherein the first laterally placed cross connector, the second laterally placed cross connector, and the at least one tulip head are positioned in separate, parallel planes in a second direction.

18. The method of claim 17 wherein the first laterally placed cross connector, the second laterally placed cross connector, and the at least one tulip head are positioned in a single plane in a third direction prior to the cross connector system being manipulated by the user.

\* \* \* \* \*